United States Patent
Fox et al.

(10) Patent No.: US 11,648,684 B2
(45) Date of Patent: May 16, 2023

(54) ROBOTIC DEVICE FOR DISTRIBUTING DESIGNATED ITEMS

(71) Applicant: X-Tend Robotics Inc., Middleburg, FL (US)

(72) Inventors: Harry Fox, Jerusalem (IL); David Azoulay, Jerusalem (IL); Sergh Sapojnikov, Ashkelon (IL)

(73) Assignee: X-Tend Robotics Inc., Middleburg, FL (US)

( * ) Notice: Subject to any disclaimer, the term of this patent is extended or adjusted under 35 U.S.C. 154(b) by 0 days.

(21) Appl. No.: 17/937,465

(22) Filed: Oct. 3, 2022

(65) Prior Publication Data

US 2023/0025372 A1     Jan. 26, 2023

Related U.S. Application Data

(62) Division of application No. 17/714,187, filed on Apr. 6, 2022, now Pat. No. 11,565,425.

(Continued)

(51) Int. Cl.
*B25J 19/02*     (2006.01)
*B25J 11/00*     (2006.01)
(Continued)

(52) U.S. Cl.
CPC .......... *B25J 11/009* (2013.01); *B25J 11/0005* (2013.01); *B25J 19/02* (2013.01);
(Continued)

(58) Field of Classification Search
CPC ......... B33Y 50/02; B33Y 30/00; B33Y 50/00; B33Y 10/00; B22F 5/00; B22F 10/20;
(Continued)

(56) References Cited

U.S. PATENT DOCUMENTS 9,489,490 B1    11/2016   Theobald
10,207,296 B2 *   2/2019   Garcia ..................... B07C 5/34
(Continued)

FOREIGN PATENT DOCUMENTS

| CN | 111267117 A | 6/2020 |
| CN | 112207838 A | 1/2021 |
| GB | 2598037 A | 2/2022 |

OTHER PUBLICATIONS

West et al., Machine Vision in Practice, 1983, IEEE, p. 794-801 (Year: 1983).*

(Continued)

*Primary Examiner* — McDieunel Marc
(74) *Attorney, Agent, or Firm* — Heidi Brun Associates Ltd.

(57) ABSTRACT

An autonomously moving robotic device for distributing designated items includes multiple compartments, a release mechanism to release items from the multiple compartments; a memory module containing optical recognition scans and personal information of persons located within a premises, and substantive information of the designated items, optical recognition scanners, a control module in communication with the optical recognition scanners, the memory and the release mechanism. The control unit directs movement of the device, directs the optical recognition scanners to scan persons, and compares images from the optical recognition scanners to optical recognitions in the memory to identify persons. Upon identifying a person, the control unit searches personal information of the person and identifies designated items specified for that person, and then directs the release mechanism to release the designated item.

21 Claims, 16 Drawing Sheets

Related U.S. Application Data

(60) Provisional application No. 63/209,003, filed on Jun. 10, 2021, provisional application No. 63/181,243, filed on Apr. 29, 2021.

(51) Int. Cl.
  *G16H 20/13* (2018.01)
  *G06F 21/32* (2013.01)
  *G06F 21/44* (2013.01)

(52) U.S. Cl.
  CPC .............. *G06F 21/32* (2013.01); *G06F 21/44* (2013.01); *G16H 20/13* (2018.01)

(58) Field of Classification Search
  CPC .. B22F 2005/001; B22F 10/30; B29C 64/386; Y02P 10/25; H04N 1/4092; B25J 5/007; B25J 11/009; B25J 11/0005; B25J 9/1694; B25J 19/023; B25J 19/04; A61J 7/0084; A61J 1/03
  See application file for complete search history.

(56) References Cited

U.S. PATENT DOCUMENTS

| | | | |
|---|---|---|---|
| 11,203,120 B1* | 12/2021 | Hill | B25J 9/0087 |
| 2001/0056311 A1 | 12/2001 | Valerino, Sr. | |
| 2004/0019406 A1 | 1/2004 | Wang | |
| 2005/0021182 A1 | 1/2005 | Wang | |
| 2010/0206651 A1* | 8/2010 | Nagasaka | B25J 5/007 |
| | | | 180/218 |
| 2015/0134106 A1 | 5/2015 | Boyer | |
| 2018/0154514 A1 | 6/2018 | Angle | |
| 2019/0381661 A1* | 12/2019 | Taira | B25J 9/162 |
| 2020/0361715 A1* | 11/2020 | Meier | F16N 9/00 |
| 2020/0411154 A1 | 12/2020 | Lee | |
| 2021/0252712 A1* | 8/2021 | Patrick | G05D 1/0212 |
| 2021/0354945 A1* | 11/2021 | Deng | B25J 19/023 |
| 2022/0126452 A1* | 4/2022 | Pennington | B25J 19/023 |

OTHER PUBLICATIONS

Illmann et al., Statistical recognition of motion patterns, 2002, IEEE, p. 1259-1269 (Year: 2002).*

Rajput et al., Alternative Product Label Reading and Speech Conversion: An Aid for Blind Person, 2017, IEEE, p. 1-6 (Year: 2017).*

Zhuang et al., 3-D-Laser-Based Scene Measurement and Place Recognition for Mobile Robots in Dynamic Indoor Environments, 2012, IEEE, p. 438-450 (Year: 2012).*

Combined Search and Examination Report for corresponding application GB2109542.7 dated Nov. 30, 2021.

International Search Report for corresponding application PCT/IB2022/053254 dated Aug. 17, 2022.

Lima et al., "Robotic telemedicine for mental health: a multimodal approach to improve human-robot engagement." Frontiers in Robotics and AI 8 (2021): 618866. Mar. 18, 2021, Retrieved on Jul. 19, 2022 from <https://www.frontiersin.org/articles/10.3389/frobt.2021.618866/full>.

Jarvis, Multimodal Robot/Human Interaction in an Assistive Technology Context, 2009, IEEE, p. 212-218 (Year: 2009).

Suthakorn et al., A robotic library system for an off-site shelving facility, 2002, IEEE, p. 3589-3594 (Year: 2002).

Miseikis et al., Lio-A Personal Robot Assistant for Human-Robot Interaction and Care Applications, 2020, IEEE, p. 5339-5346 (Year: 2020).

Choi et al., Robotic laboratory automation platform based on mobile agents for flexible clinical tests, 2010, IEEE, p. 186-191 (Year: 2010).

* cited by examiner

ROBOTIC DEVICE FOR DISTRIBUTING DESIGNATED ITEMS

CROSS-REFERENCE TO RELATED APPLICATIONS

This application is a divisional application of U.S. Ser. No. 17/714,187, which claims priority from U.S. provisional patent applications No. 63/181,243, filed Apr. 29, 2021, and 63/209,003, filed Jun. 10, 2021 all of which are incorporated herein by reference.

FIELD OF THE INVENTION

This invention pertains to the field of robotics, and, in particular, to a robotic device for distributing designated items, such as medication.

BACKGROUND OF THE INVENTION

There are stand-alone stationary devices in in the market that issue alerts that it is time to take medication. These cue someone to go and take the medication. Also very common are boxes or containers with marked compartments, so someone knows which medicine to take at a particular time.

Stand-alone automatic pill dispensers exist in the market. By activating a program and then pushing a button, the required medicine can be accessed. Some of these dispensers automatically send alerts about the need to take a specified medication. Further, some are connected to the Internet, or a local network, so they can be remotely activated to dispense medication.

Pria has a mobile app that alerts you when it is time to take a prescribed medication. https://www.okpria.com/How-it-works The user then goes to the Pria pill wheel and is recognized by facial recognition and the medication can then be received from the pill wheel.

All of these medication dispensers, however, are stationary. They do not move. Therefore, there is a need in the industry for a "smart" mobile medication dispenser that can identify people and then dispense their specified medication.

Accordingly, there is a need in the industry for a robotic device that can efficiently and effectively distribute items, such as medication.

SUMMARY OF THE INVENTION

To achieve these and other objects, the herein robotic device can efficiently and effectively distribute items, such as medication. In particular, it embodies a "smart" mobile medication dispenser that can identify people and then dispense their specified medication. It has particular application in medical centers, nursing facilities, assisted living centers and similar facilities, wherein a myriad of people need to be given their specified prescribed medication at specified times.

Therefore, to achieve these and other objects, the herein disclosed invention is a robotic device for distributing designated items to designated persons, comprising: means for autonomously moving the robotic device through a premises; storage means including multiple compartments for containing designated items; means for dispensing items from the storage means; an external or internal memory module containing optical recognition scans and personal information of persons located within the premises, and substantive information of the designated items; optical recognition scanners; a control module in electronic communication with the means for autonomously moving, the optical recognition scanners, the memory and the means for dispensing; and, where, the control unit directs the means for autonomously moving to move the robotic device within the premises, directs the optical recognition scanners to scan persons as they are encountered, compares images from the optical recognition scanners to optical recognitions in the memory to identify the person; and, where, upon identifying the person, the control unit searches the personal information of the person in the memory and identifies designated items specified for the person, and then directs the means for dispensing to dispense the designated item to the person.

The system enables management of pills by supporting functions, such as retrieval, scheduled distribution, analysis, and notifications. This system also includes the identification of pills through optical sensors and weight measurement devices that can detect, e.g., a texture, a shape, and a size of pills. Such identification can be used to program retrieval attempts by a retrieval robot and in the formulation of the retrieval pattern. Additionally, networked notification systems for pills can be used for updating rules or schedules related to the dispensable units or alerting users and remote resources of any potential misuse or hazards of the dispensable units.

The system supports any solid pill shape, size, and texture. To avoid contamination, the system does not work with gummies or powders. If desired, the system can be adapted to support liquid medications. It preferably contains 55 cartridges, thereby supporting up to 55 different pills that can be distributed at any given time/patient.

In additional to the pill distribution, the system may preferably include a disposable paper cup maker and/or dispenser.

The dispenser can preferably be integrated with robotic systems, which allows support of high-level medication distribution management and monitoring. For an example: only authorized personal (e.g., care giver, pharmacist, nurse, doctor) have access and can fill the cartridges with pills. This can be accomplished by face and object recognition subsystem in the robotic delivery system. The system supports real-time access to NDC database of medications and checks NDC and FDA regulations in additional to a doctor's recommended prescription.

There is provided, in accordance with a preferred embodiment of the present invention, a robotic device for distributing designated items to designated persons. The robotic device includes means for autonomously moving the robotic device through a premises; storage means including multiple compartments for containing designated items; means for dispensing items from the storage means; an external or internal memory module containing optical recognition scans and personal information of persons located within the premises, and substantive information of the designated items; optical recognition scanners; a control module in electronic communication with the means for autonomously moving, the optical recognition scanners, the memory the means for dispensing; and where the control unit directs the means for autonomously moving to move the robotic device within the premises, directs the optical recognition scanners to scan persons as they are encountered, compares images from the optical recognition scanners to optical recognitions in the memory to identify the person. Upon identifying the person, the control unit searches the personal information of the person in the memory and identifies designated items specified for the person, and then directs the means for dispensing to dispense the designated item to the person; and where the means for dispensing items from the storage means including a movable vacuum tube, a controlled vacuum, a mobile arm for controlled movement of the vacuum tube and an exit tube, where the storage means rotates until a compartment for the designated item is in alignment with the vacuum tube, the controlled vacuum is activated and the designated item is sucked into the vacuum tube and held, the mobile arm moves the vacuum tube until it aligns with the exit tube, and the vacuum is deactivated and the designated item falls through the exit tube.

Moreover, in accordance with a preferred embodiment of the present invention, the designated items are pharmaceutical products.

Further, in accordance with a preferred embodiment of the present invention, the device also includes secondary recognition scanners; and, the memory module further containing secondary recognition scans of persons located within the premises; and, wherein, prior to dispensing the designated item, the control unit directs the secondary recognition scanners to scan the person, compares images from the secondary recognition scanners to secondary recognitions in the memory to confirm the person is the correct person to receive the designated item.

Still further, in accordance with a preferred embodiment of the present invention, the secondary recognition scanners being magnetic code readers, fingerprint scanners or eye scanners or facial scanners or optical scanners and the secondary recognition scans of persons located within the memory being magnetic codes, fingerprint scans or eye scans or facial scans or optical scans.

Additionally, in accordance with a preferred embodiment of the present invention, the means for dispensing further includes substantive scanners and the memory module further containing substantive scans of the designated items; and, where, prior to dispensing the designated item, the control unit directs the substantive scanners to scan the designated item, compares scans from the substantive scanners to substantive scans in the memory to confirm the designated item is the correct designated item for the person.

Moreover, in accordance with a preferred embodiment of the present invention, the storage means further includes supplemental recognition scanners; and, the memory module further containing supplemental recognition scans of persons authorized to add items to the storage means; and, where, prior to adding items to the storage means, the control unit directs the supplemental scanners to scan persons attempting to add items to the storage means, compares scans from the supplemental scanners to supplemental scans in the memory to confirm the persons attempting to add items to the storage means are authorized to add items to the storage means.

There is provided, in accordance with a preferred embodiment of the present invention, a mobile robot device for distributing designated items. The mobile robot device includes a memory module storing person images each with an associated identification and information on associated designated items for at least one person, a first optical recognition scanner to scan and to provide an image of an encountered person as the mobile robot device approaches the encountered person; a control unit to compare images from the first optical recognition scanner with the person images and to identify the encountered person and their associated designated items accordingly; a second optical scanner to scan and provide an image of the encountered person for the control unit to confirm that the identified encountered person is the correct person to receive the associated designated items; a release mechanism to release the associated designated items according to the encountered person identification; a third optical recognition scanner to scan the released associated designated items for the control unit to check that the scanned released designated items are the correct associated designated items for the encountered person before the release mechanism dispenses the associated designated items to the encountered person.

There is provided, in accordance with a preferred embodiment of the present invention, a device for dispensing designated items integrated with a mobile robot device, the device includes at least one storage compartment storing designated items; at least one scanner to scan to scan and to provide an image of an encountered person as the mobile robot device approaches the encountered person; a vacuum tube to suck designated items out of the at least one storage compartment; a control unit to compare images from the at least one with the person images and to identify the encountered person and their associated designated items accordingly, the control unit to direct the vacuum tube to the at least one storage compartment according to the associated designated items and to activate a vacuum in the vacuum tube; a mobile arm to move the vacuum tube from the at least one storage compartment to an exit tube and to indicate to the control unit to release the associated items into the exit tube; a scanner to scan the released associated designated items for the control unit to check that the scanned released designated items are the correct associated designated items for the encountered person; and a container to receive the designated items from the exit tube.

There is provided, in accordance with a preferred embodiment of the present invention, a robotic device for distributing designated items to designated persons. The robotic device includes means for autonomously moving the robotic device through a premises; storage means including multiple compartments for containing designated items; means for dispensing items from the storage means; an external or internal memory module containing optical recognition scans and personal information of persons located within the premises, and substantive information of the designated items; optical recognition scanners; a control module in electronic communication with the means for autonomously moving, the optical recognition scanners, the memory and the means for dispensing; and where the control unit directs the means for autonomously moving to move the robotic device within the premises, directs the optical recognition scanners to scan persons as they are encountered, compares images from the optical recognition scanners to optical recognitions in the memory to identify the person; and where upon identifying the person, the control unit searches the personal information of the person in the memory and identifies designated items specified for the person, and then directs the means for dispensing to dispense the designated item to the person; and the device further including secondary recognition scanners; and, the memory module further containing secondary recognition scans of persons located within the premises; and, where prior to dispensing the designated item, the control unit directs the secondary recognition scanners to scan the person, compares images from the secondary recognition scanners to secondary recognitions in the memory to confirm the person is the correct person to receive the designated item.

There is provided, in accordance with a preferred embodiment of the present invention, a robotic device for distributing designated items to designated persons. The device includes means for autonomously moving the robotic device through a premises; storage means including multiple compartments for containing designated items; means for dispensing items from the storage means; an external or internal memory module containing optical recognition scans and personal information of persons located within the premises, and substantive information of the designated items; optical recognition scanners; a control module in electronic communication with the means for autonomously moving, the optical recognition scanners, the memory and the means for dispensing; and where the control unit directs the means for autonomously moving to move the robotic device within the premises, directs the optical recognition scanners to scan persons as they are encountered, compares images from the optical recognition scanners to optical recognitions in the memory to identify the person; and where, upon identifying the person, the control unit searches the personal information of the person in the memory and identifies designated items specified for the person, and then directs the means for dispensing to dispense the designated item to the person; and where the means for dispensing further includes substantive scanners and the memory module further containing substantive scans of the designated items; and, where prior to dispensing the designated item, the control unit directs the substantive scanners to scan the designated item, compares scans from the substantive scanners to substantive scans in the memory to confirm the designated item is the correct designated item for the person.

There is provided, in accordance with a preferred embodiment of the present invention, a robotic device for distributing designated items to designated persons. The robotic device includes means for autonomously moving the robotic device through a premises, storage means including multiple compartments for containing designated items; means for dispensing items from the storage means; an external or internal memory module containing optical recognition scans and personal information of persons located within the premises, and substantive information of the designated items; optical recognition scanners; a control module in electronic communication with the means for autonomously moving, the optical recognition scanners, the memory and the means for dispensing; and, where, the control unit directs the means for autonomously moving to move the robotic device within the premises, directs the optical recognition scanners to scan persons as they are encountered, compares images from the optical recognition scanners to optical recognitions in the memory to identify the person; and, where, upon identifying the person, the control unit searches the personal information of the person in the memory and identifies designated items specified for the person, and then directs the means for dispensing to dispense the designated item to the person; and where the storage means further includes supplemental recognition scanners; and, the memory module further containing supplemental recognition scans of persons authorized to add items to the storage means; and where prior to adding items to the storage means, the control unit directs the supplemental scanners to scan persons attempting to add items to the storage means, compares scans from the supplemental scanners to supplemental scans in the memory to confirm the persons attempting to add items to the storage means are authorized to add items to the storage means.

Moreover, in accordance with a preferred embodiment of the present invention, the designated items are pharmaceutical products.

Further, in accordance with a preferred embodiment of the present invention, the device further includes secondary recognition scanners; and, the memory module further containing secondary recognition scans of persons located within the premises; and, where prior to dispensing the designated item, the control unit directs the secondary recognition scanners to scan the person, compares images from the secondary recognition scanners to secondary recognitions in the memory to confirm the person is the correct person to receive the designated item.

Additionally, in accordance with a preferred embodiment of the present invention, the secondary recognition scanners being magnetic code readers, fingerprint scanners or eye scanners or facial scanners or optical scanners and the secondary recognition scans of persons located within the memory being magnetic codes, fingerprint scans or eye scans or facial scans or optical scans.

Moreover, in accordance with a preferred embodiment of the present invention, the means for dispensing further includes substantive scanners and the memory module further containing substantive scans of the designated items; and, where, prior to dispensing the designated item, the control unit directs the substantive scanners to scan the designated item, compares scans from the substantive scanners to substantive scans in the memory to confirm the designated item is the correct designated item for the person.

Further, in accordance with a preferred embodiment of the present invention, the storage means further includes supplemental recognition scanners; and, the memory module further containing supplemental recognition scans of persons authorized to add items to the storage means; and, where, prior to adding items to the storage means, the control unit directs the supplemental scanners to scan persons attempting to add items to the storage means, compares scans from the supplemental scanners to supplemental scans in the memory to confirm the persons attempting to add items to the storage means are authorized to add items to the storage means.

BRIEF DESCRIPTION OF THE FIGURES

For a better understanding of the invention and to show how it may be carried into effect, reference will now be made, purely by way of example, to the accompanying Figures, wherewith it is stressed that the particulars shown are by way of example and for purposes of illustrative discussion of the preferred embodiments of the present invention only, and are presented in the cause of providing what is believed to be the most useful and readily understood description of the principles and conceptual aspects of the invention.

DETAILED DESCRIPTION OF THE INVENTION

Figure 1:
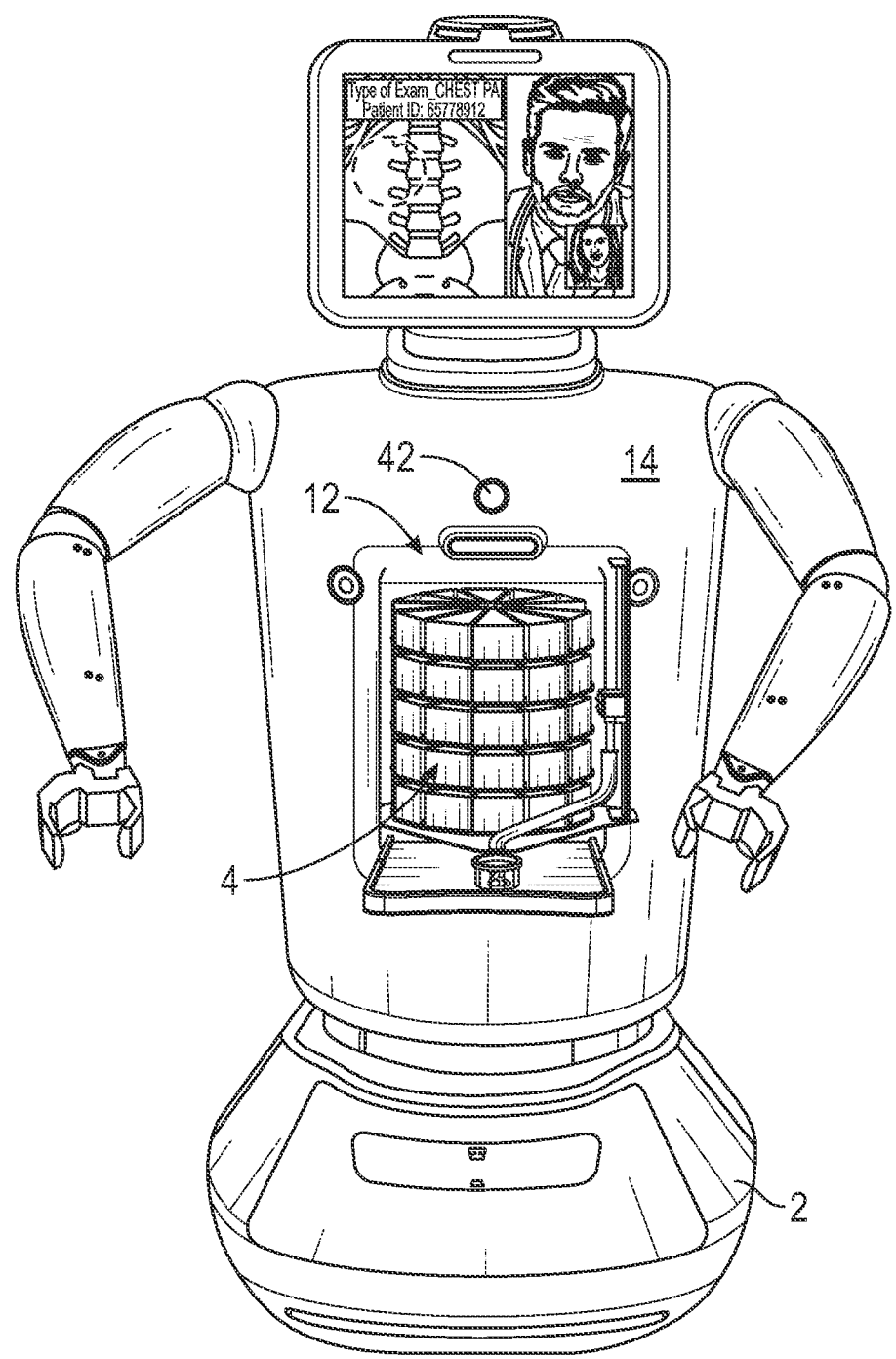
FIG. 1 is a front view of a robotic device containing a medication dispenser; constructed and operative in accordance with the present invention.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

According to the broadest definition of the Invention, it pertains to a robotic device for distributing designated items to designated persons, comprising:

Means for autonomously moving said robotic device through a premises;

Storage means including multiple compartments for containing designated items;

Means for dispensing items from said storage means;

An external or internal memory module containing optical recognition scans and personal information of persons located within said premises, and substantive information of said designated items;

Optical recognition scanners;

A control module in electronic communication with said means for autonomously moving, said optical recognition scanners, said memory and said means for dispensing; and, Wherein, said control unit directs said means for autonomously moving to move said robotic device within said premises, directs said optical recognition scanners to scan persons as they are encountered, compares images from said optical recognition scanners to optical recognitions in said memory to identify said person; and, Wherein, upon identifying said person, said control unit searches said personal information of said person in said memory and identifies designated items specified for said person, and then directs said means for dispensing to dispense said designated item to said person.

In a preferred embodiment, the designated items are pharmaceutical products and the robot is preferably used to distribute medication to residents and patents in hospitals, medical centers and elder care facilities.

According to the invention, the robot autonomously moves through the premises. When it encounters a person, it takes an optical scan of that person. It searches to see if that person is in memory. If there is a match, the memory identifies the medication for that person.

The means for dispensing can be any suitable electro-mechanical device. In one embodiment, it involves a movable vacuum tube. The storage means rotates—or otherwise moves, until the compartment for the designated medicine is in alignment with the vacuum tube attached to a mobile arm. By means of a controlled vacuum, the medicine is sucked into the vacuum tube and held. The mobile arm then moves the vacuum tube until it aligns with an exit tube. At this point, the vacuum is deactivated and the medicine falls through the exit tube.

At the bottom of the exit tube, a cup [or other catching element] receives the medicine. The designated patient may then take the cup with the medicine.

According to a preferred embodiment, the device may additionally include secondary recognition scanners; and, said memory module further containing secondary recognition scans of persons located within said premises; and, wherein, prior to dispensing said designated item, said control unit directs said secondary recognition scanners to scan said person, compares images from said secondary recognition scanners to secondary recognitions in said memory to confirm said person is the correct person to receive said designated item.

To ensure that the patient taking the medicine is in fact the correct person for that medicine, additional scanners may be provided at the point where the cup and medicine is located. This way there is additional protection to prevent the wrong person from getting the medicine.

For additional protection, said means for dispensing further comprising substantive scanners and said memory module further containing substantive scans of said designated items; and, wherein, prior to dispensing said designated item, said control unit directs said substantive scanners to scan said designated item, compares scans from said substantive scanners to substantive scans in said memory to confirm said designated item is the correct designated item for said person.

By this means, there can be better assurance that the correct medicine was selected.

It may be appreciated that while the preferred use is for distribution of medicine, any objects may be distributed to any collection of persons. For example, designated toys can be delivered to designated children.

The storage means including multiple compartments for containing designated items; and the means for dispensing items from said storage means may preferably be made as a single unitary unit. In any suitable manner it may be mounted on the robot. One possible way to mount them would be to affix them to a drawer or shelf that slides into and out of the robot.

In a preferred embodiment, the robotic medication dispenser can store and automatically dispense up to 60 different medications, including:

PRN Medications.

Controlled substances.

Multiple Security Protocols may be incorporated into the robotic device.

Face Recognition.

Bar Code Scanning.

Finger Print Verification.

Estimated Module Dimensions: 370×270×590 mm.

Capacity: 55 pill cartridge compartments.

Pill Size: Supports any pill size and shape.

User Support: Virtually unlimited users per device.

Regulations: The materials meet the requirements of FDA.

A preferred embodiment of the robotic device for distributing designated items to designated persons is illustrated in FIGS. 1-17 herein.

Figure 2:
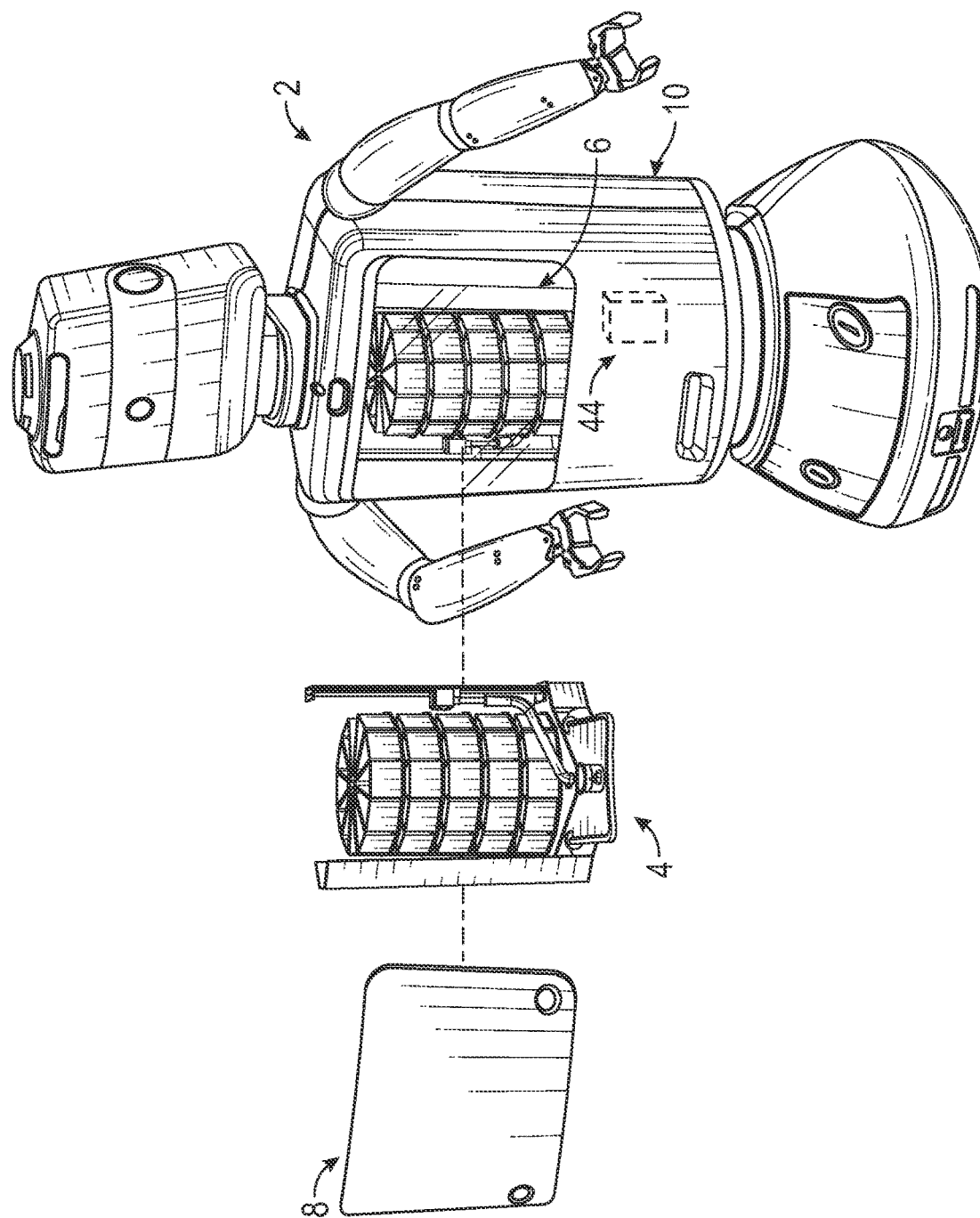
FIG. 2 is a rear perspective exploded view showing the medication dispenser inserted into the robotic device constructed and operative in accordance with the present invention.
Figure 3:
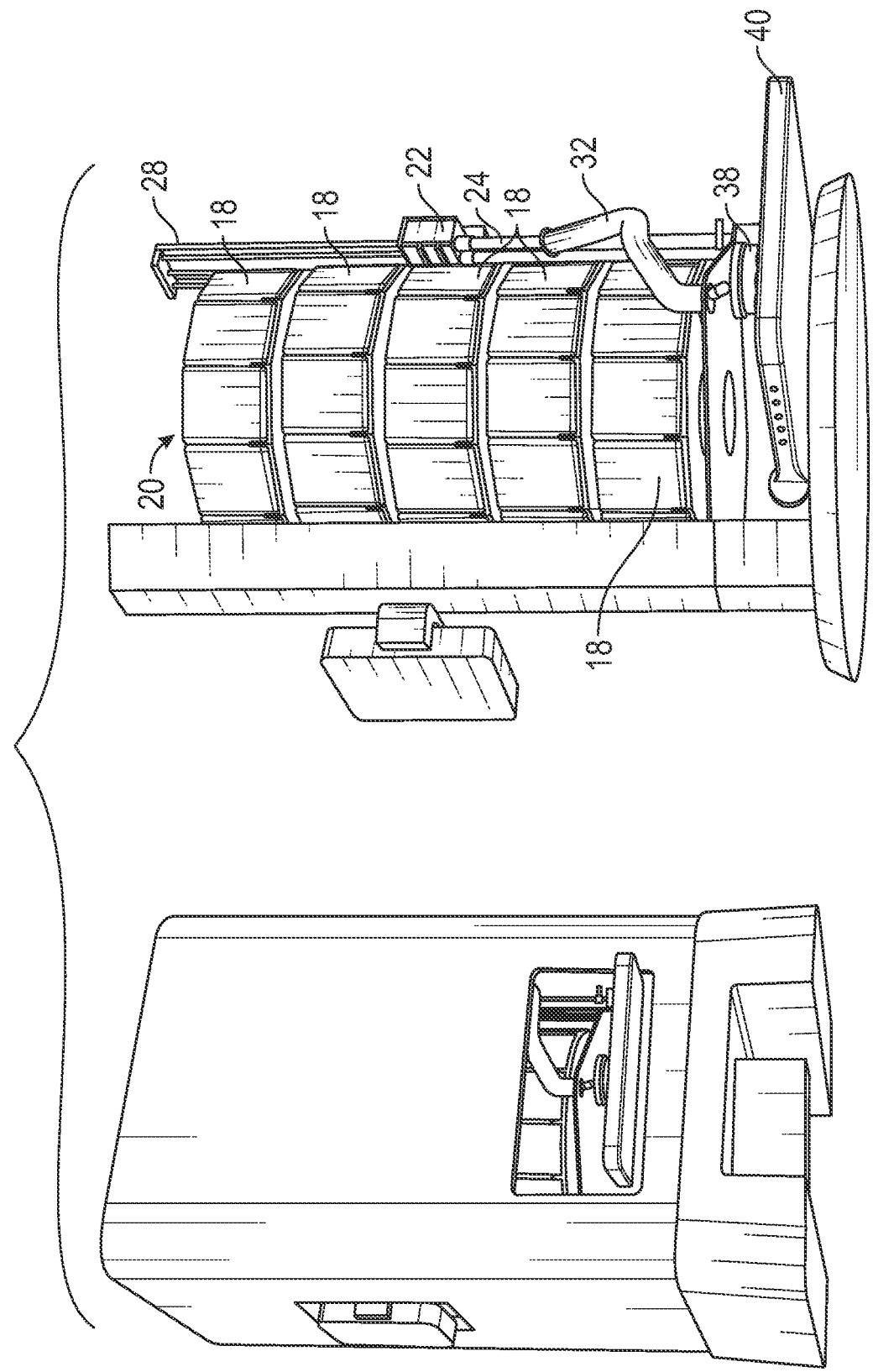
FIG. 3 is an enlarged perspective view, showing the medication dispenser and its housing, constructed and operative in accordance with the present invention.
Figure 4:
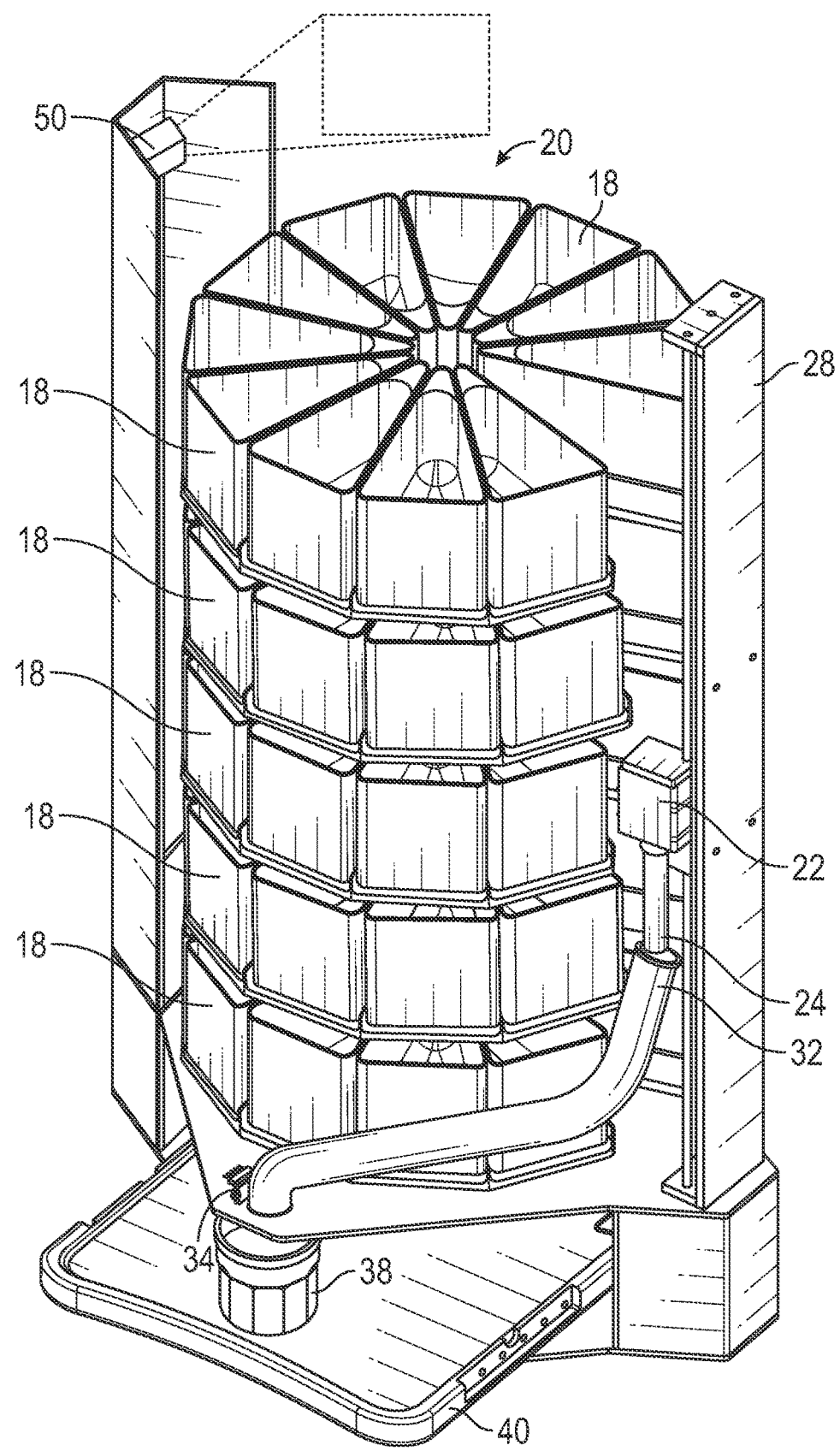
FIG. 4 is a front perspective view of the medication dispenser.
Figure 5:
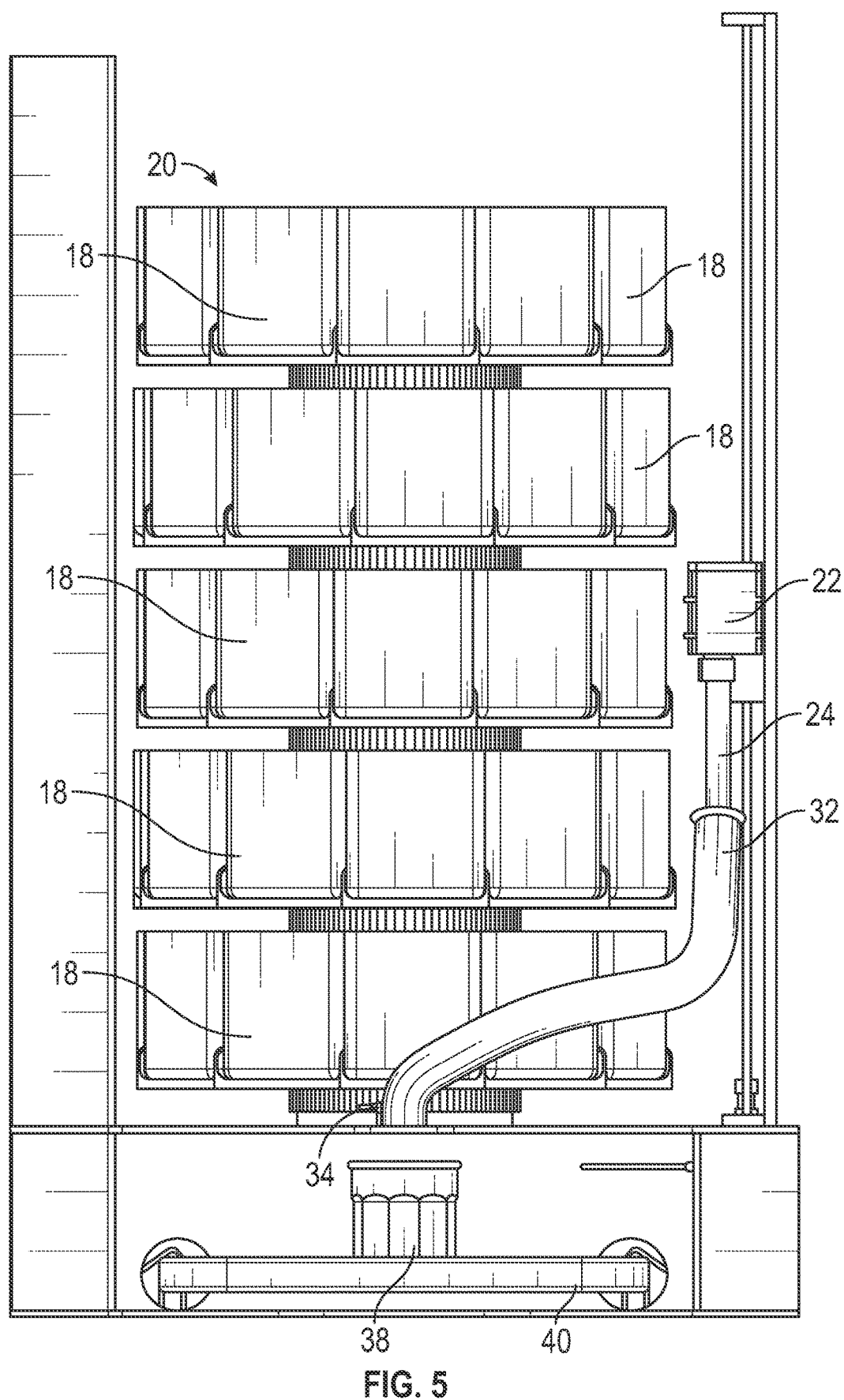
FIG. 5 is front view of the medication dispenser, constructed and operative in accordance with the present invention.
Figure 6:
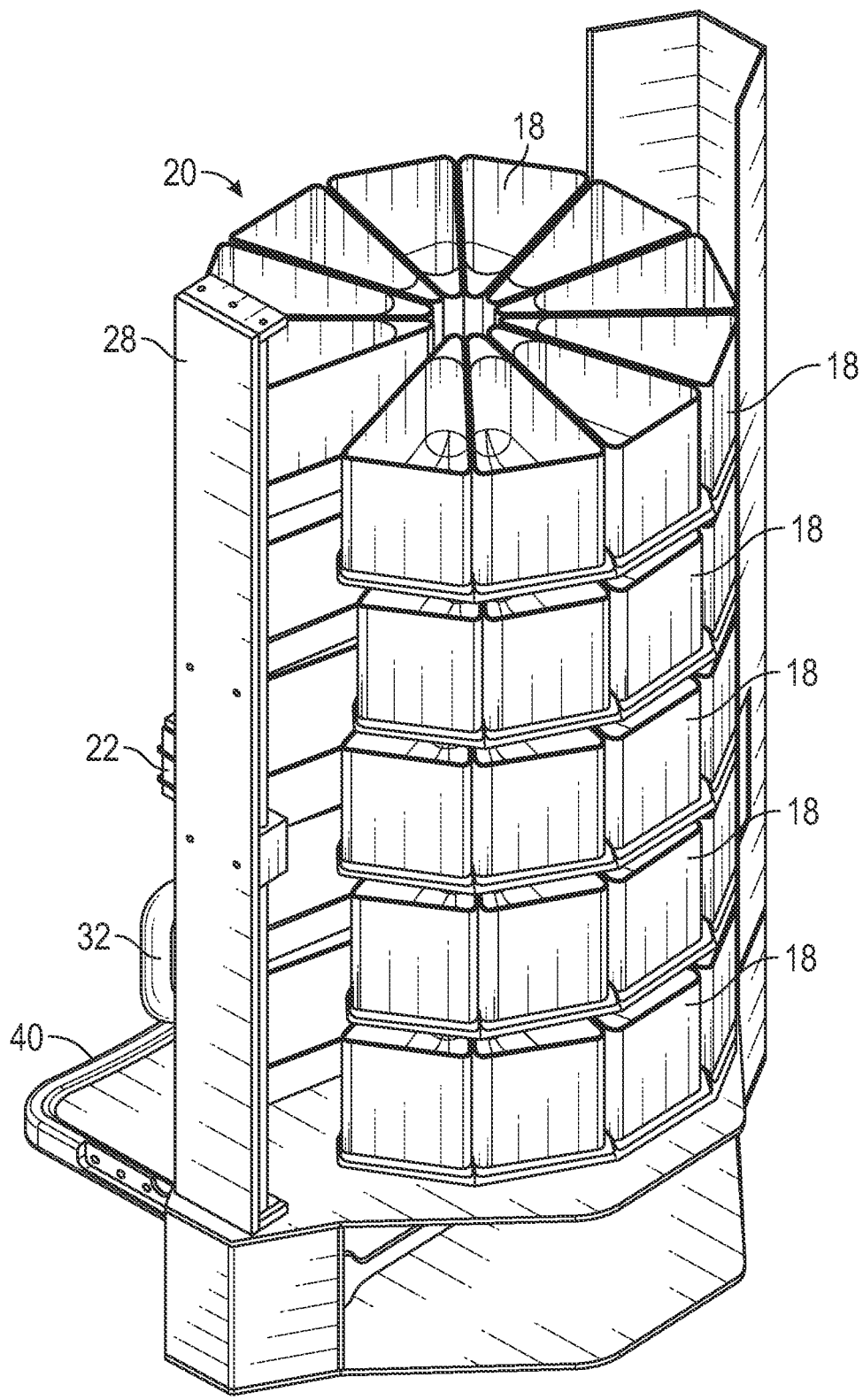
FIG. 6 is a rear perspective view of the medication dispenser, constructed and operative in accordance with the present invention.
Figure 7:
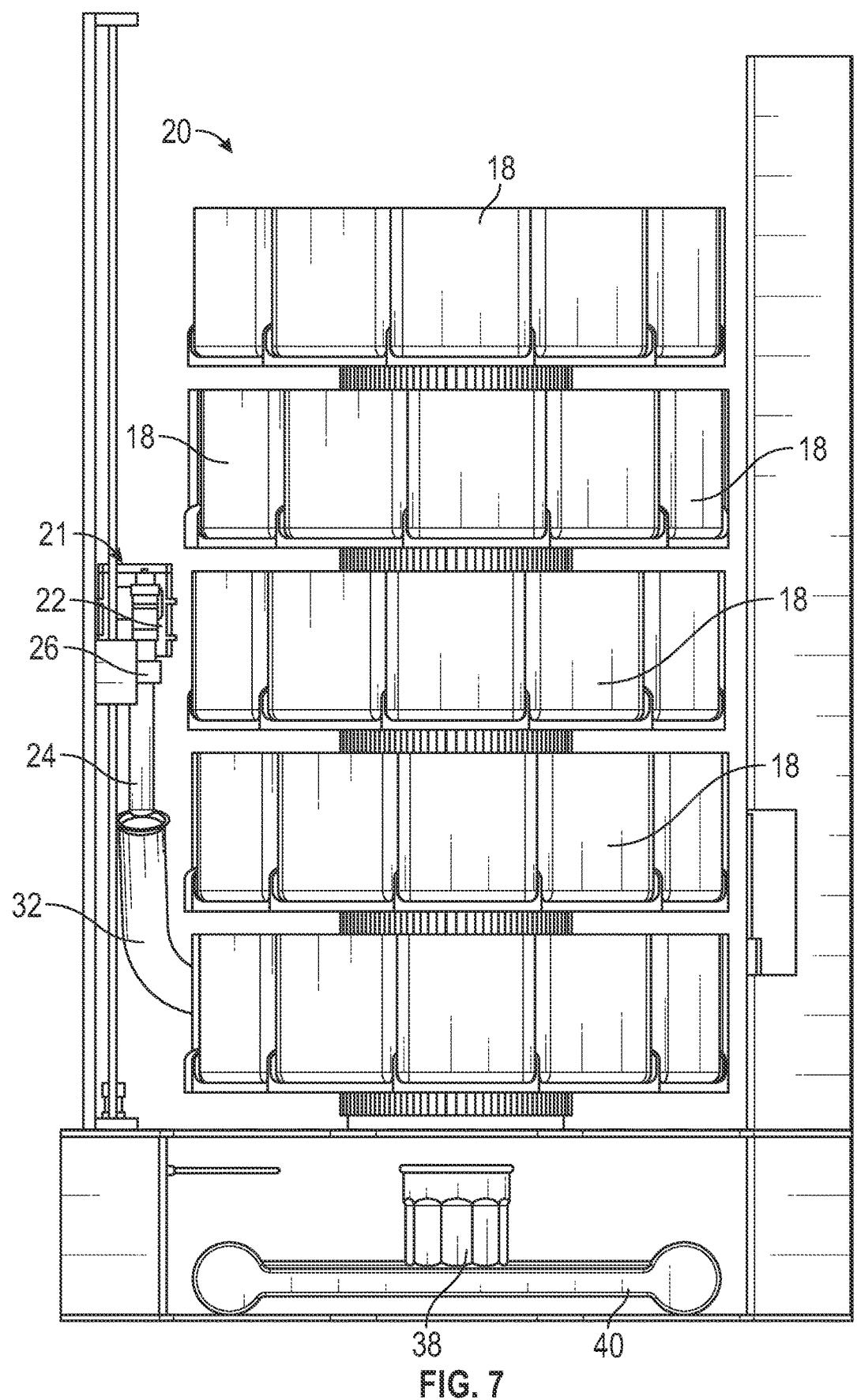
FIG. 7 is a rear view of the medication dispenser, constructed and operative in accordance with the present invention.
Figure 8:
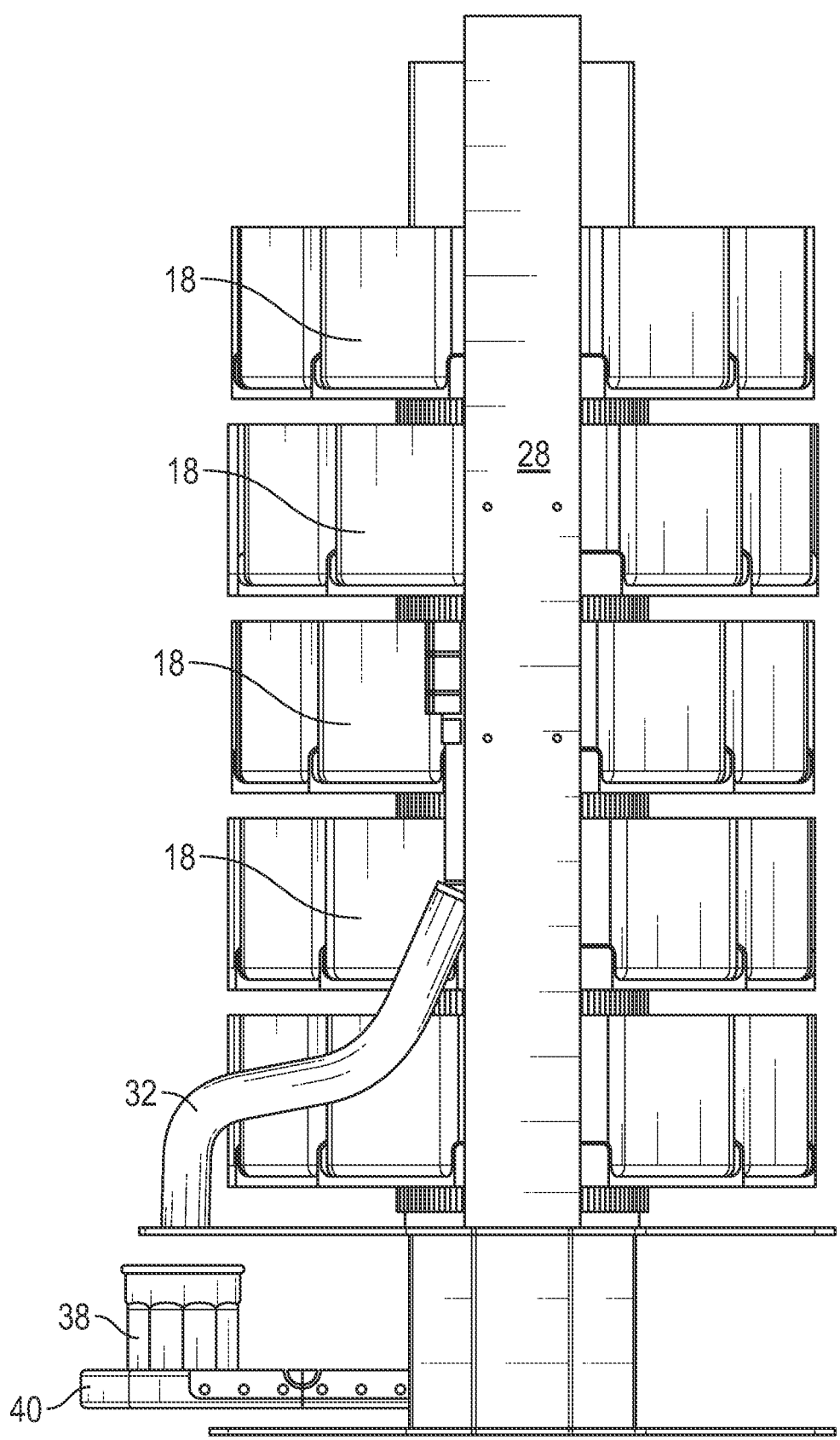
FIG. 8 is a right-side view of the medication dispenser, constructed and operative in accordance with the present invention.
Figure 9:
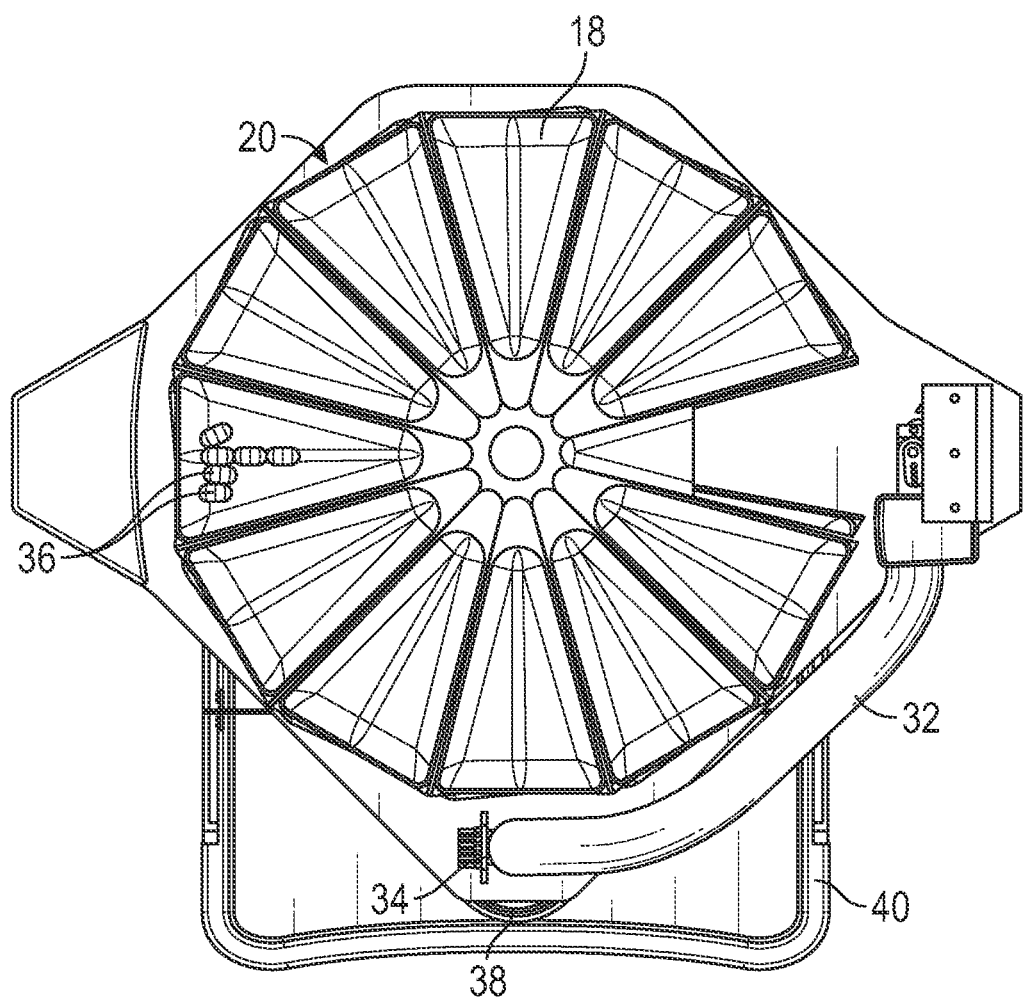
FIG. 9 is a top view of the medication dispenser, constructed and operative in accordance with the present invention.
Figure 10:
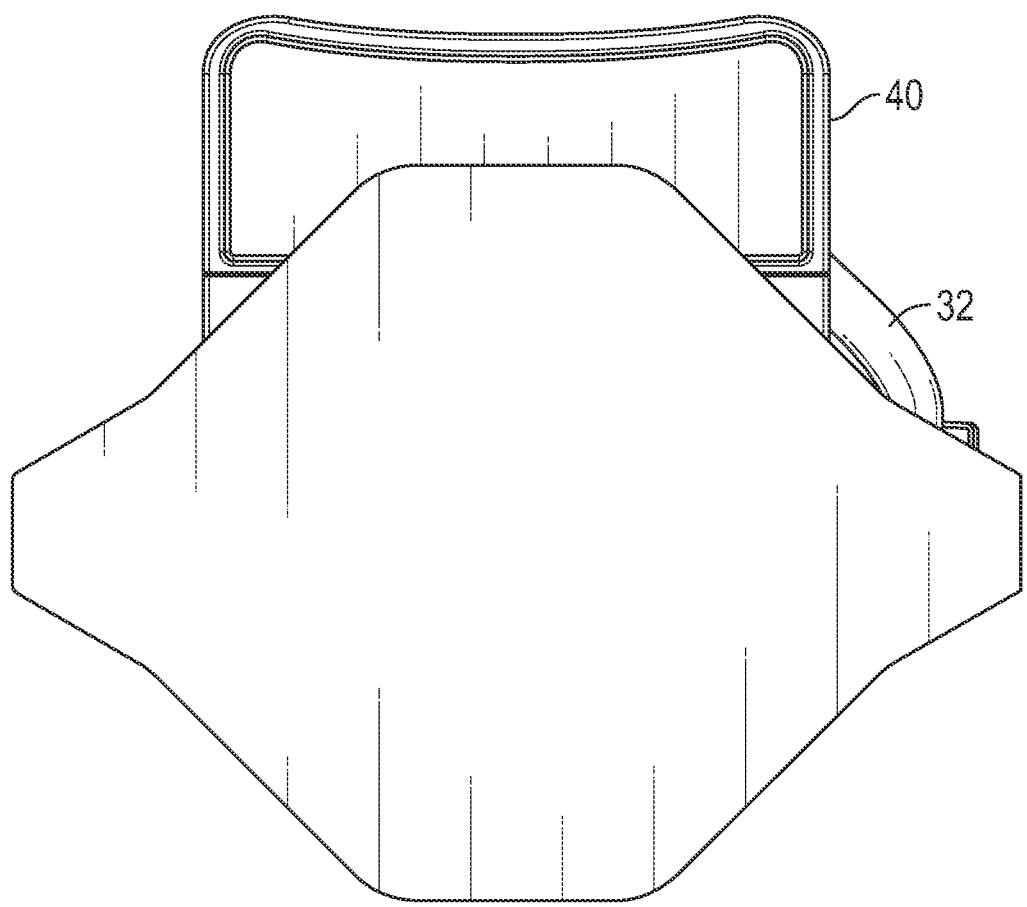
FIG. 10 is a bottom view of the medication dispenser, constructed and operative in accordance with the present invention.

Any standard or conventional robot 2 can house the dispenser 4 within an internal cavity 6 of the robot—see FIGS. 1-2. A cover 8 on the rear surface 10 of the robot may enclose the dispenser 4 to prevent damage or tampering. An opening 12 in the front torso 14 of the robot permits access to the selected medication. If desired, the front torso 14 of the robot can have an opening 12 to expose all or most of the dispenser (FIG. 1) or closed to seal the dispenser inside the robot except for an exit opening 16 (FIG. 3).

The robot includes a means for autonomously moving said robotic device through a premises. In other words, the robot is controlled by an AI process that allows the robot to direct itself through the premises without external guidance.

In the preferred embodiment, the storage means includes multiple compartments 18 for containing designated items as constituted by the dispenser 4. As shown the dispenser has any suitable shape and size. The specific shape and size are dependent on the number of medications that are to be contained within. In a preferred embodiment, the dispenser can be multi-level carousel 20 with compartments 18 and rotating about a central rod.

The means for dispensing items from said storage means may be constructed as a movable vacuum tube. A motor moves the vacuum tube vertically along a track running alongside the dispenser. When a medication and its location is identified, the vacuum motor is moved to the vertical level corresponding to the compartment in which the medication is contained. Then, the dispenser is rotated until the compartment containing the medication is in alignment with the vacuum tube. The vacuum is activated to pull the medication out of the compartment and to hold it in the vacuum tube. By means of the motor the vacuum tube is moved until it is in alignment with the exit tube. The vacuum is deactivated and the medication falls through the exit tube to be accessible to the recipient.

Figure 11:
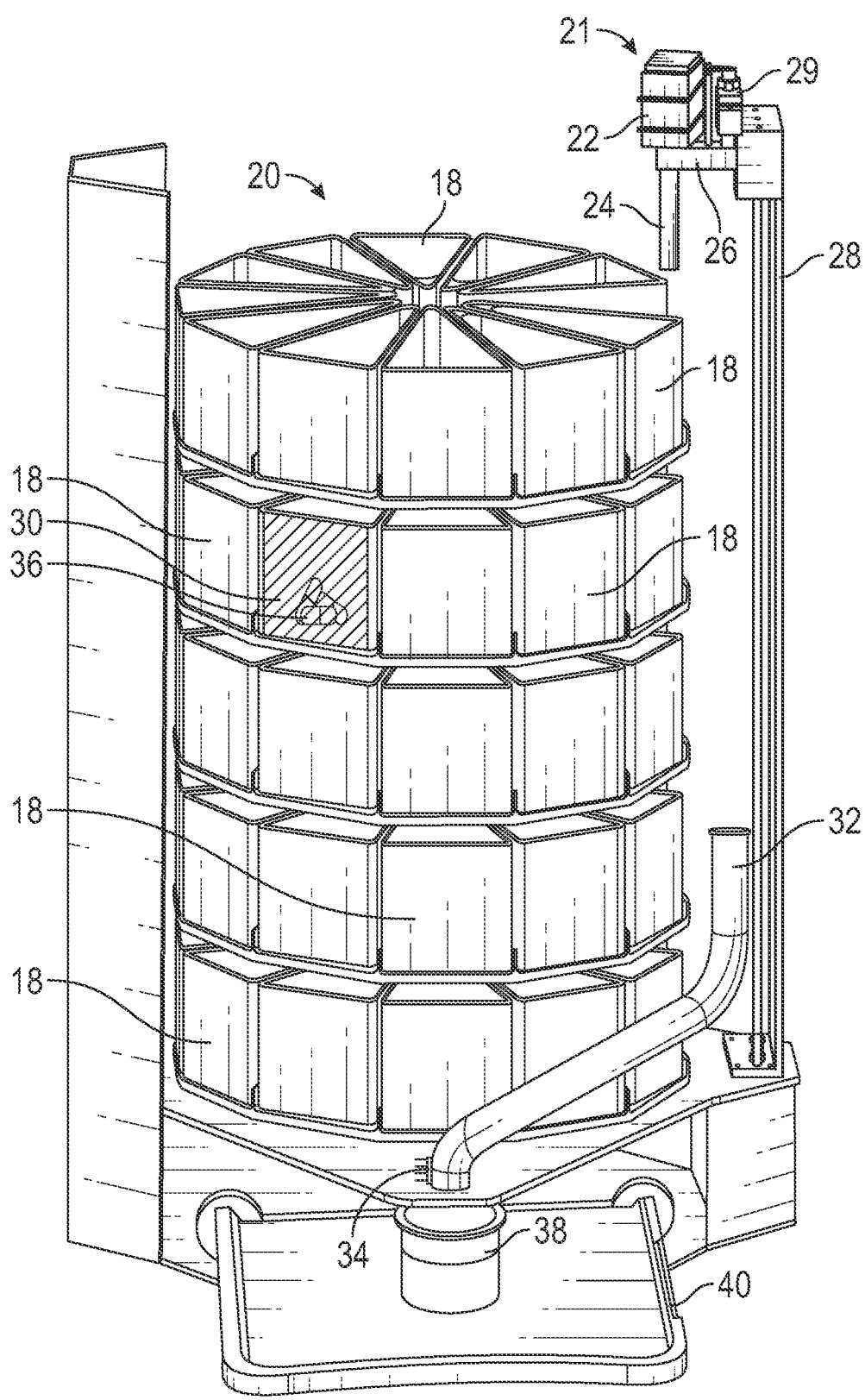
FIG. 11 is a front perspective of the medication dispenser and showing all the elements of the extraction device, constructed and operative in accordance with the present invention.

As shown in FIG. 11, the means for dispensing includes an extraction device 21 including a vacuum pump 22 and an accompanying vacuum tube 24. They are supported on a platform 26 that travels along a guide rail 28. A motor 29 energizes the vacuum pump 22 during operation. When not in use, the extraction device rests near the top of the guide rail 28 above the carousel 20.

In a preferred embodiment, the multi-level carousel 20 has five levels with fifty-five compartments 18—eleven compartments per level. One vertical column of compartments is empty with no compartments and is a clear unobstructed column as hereinafter described.

Figure 12:
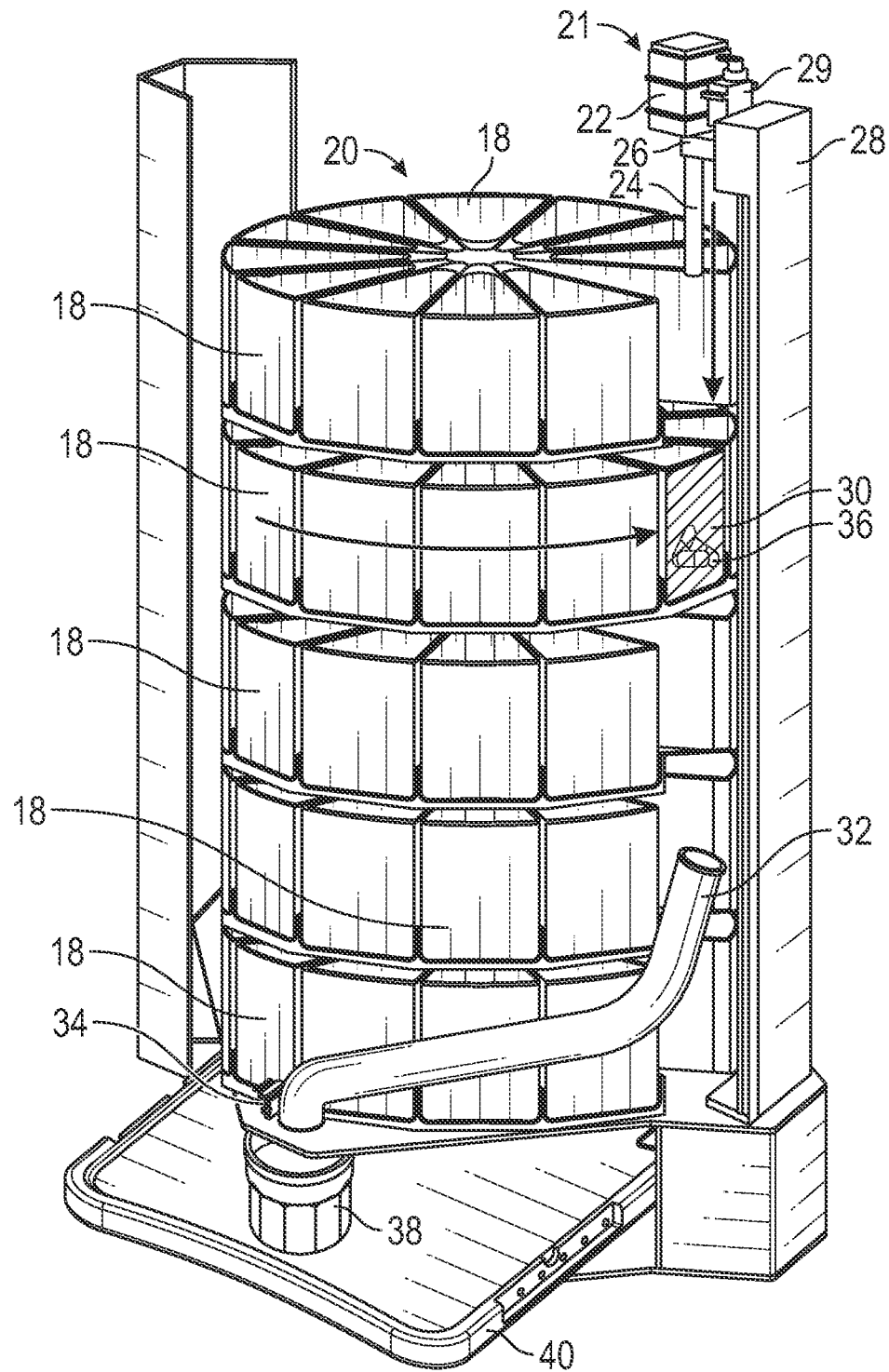
FIG. 12 is a front perspective of the medication dispenser and showing all the elements of the extraction device and the compartment with the medication constructed and operative in accordance with the present invention.
Figure 13:
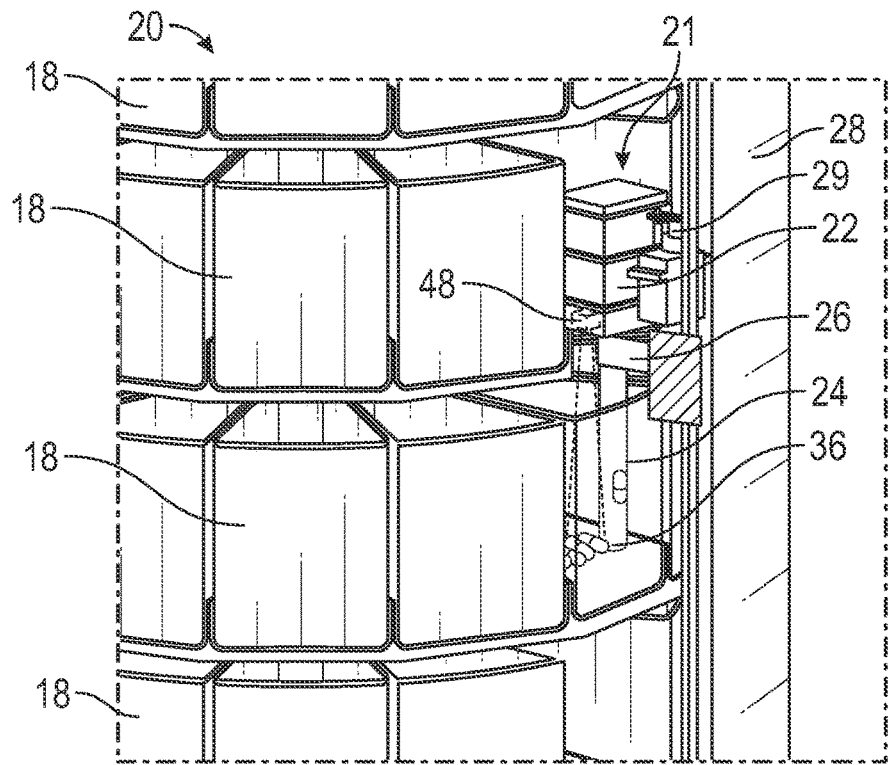
FIG. 13 is an enlarged front view of a portion of the medication dispenser and showing the extraction device coming into engagement with the compartment with the medication, constructed and operative in accordance with the present invention.

The compartment 30 with the specified medication is identified—highlighted in FIGS. 11 and 12.

As seen in FIG. 12, the carousel rotates until the compartment 30 is in vertical alignment with the vacuum tube 24. The extraction device 21 is lowered along the rail 28 until the vacuum tube 24 engages the target compartment 30— FIG. 13. Then, the vacuum motor 29 is activated to create a vacuum and the medication is sucked into to the vacuum tube 24.

Figure 14:
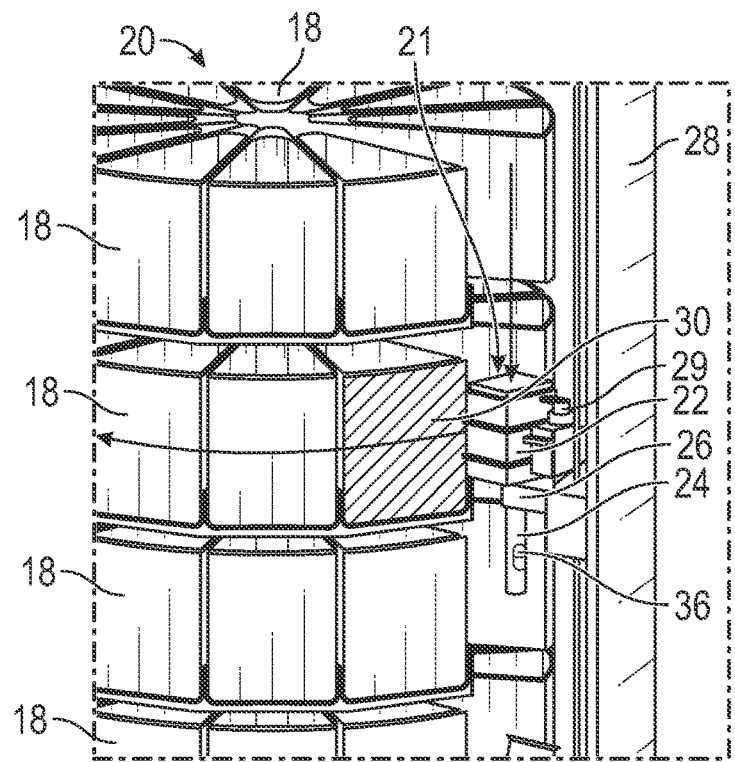
FIG. 14 is an enlarged front view of a portion of the medication dispenser and showing the extraction device extracting the medication from the compartment, constructed and operative in accordance with the present invention.
Figure 15:
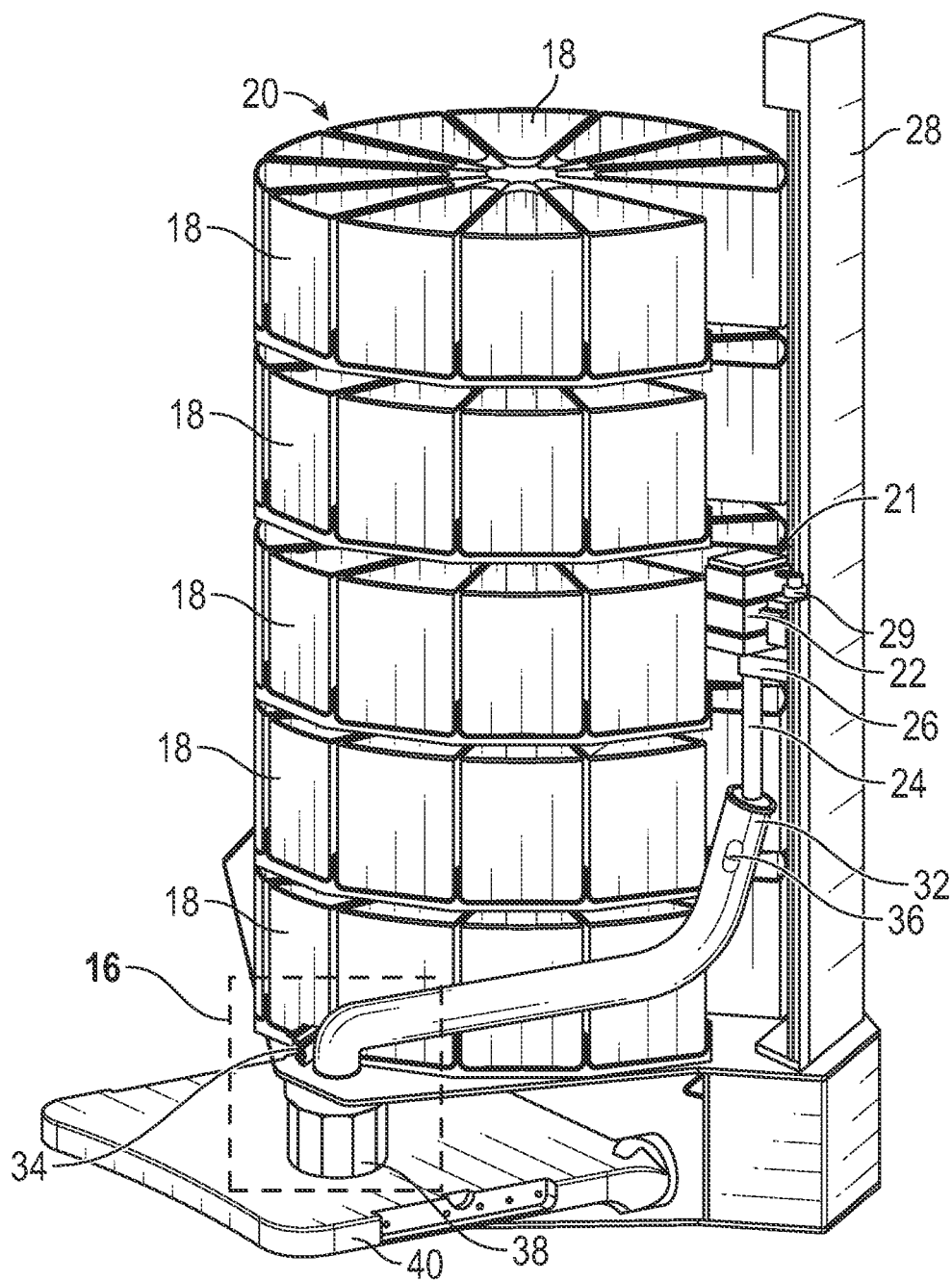
FIG. 15 is front perspective view of the medication dispenser and showing the extraction device traveling through the exit tube, constructed and operative in accordance with the present invention.

The carousel is rotated until the extraction device 21 is clear of the target compartment 30 and is contained within a clear column— FIG. 14. The extraction device 21 is lowered until the vacuum tube 24 is in juxtaposition with the exit tube 32. As shown in FIG. 15, the extraction device is partially rotated until the vacuum tube aligns with the exit tube. The motor 29 is deactivated and the vacuum pump 22 stops. This terminates the vacuum and the medication drops into the exit tube 32.

Figure 16:
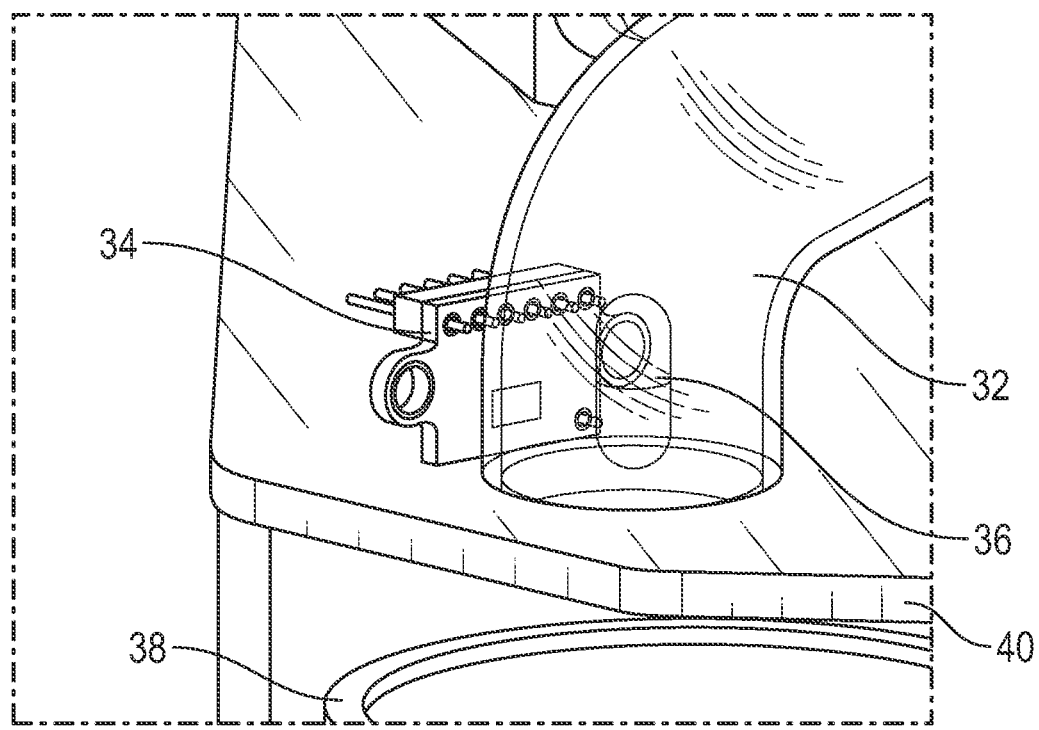
FIG. 16 is an enlarged front view of a portion of the medication dispenser and showing the exit tube with the composition sensor, constructed and operative in accordance with the present invention.

In a preferred embodiment—as shown in FIG. 16, near the bottom of the exit tube 32, a composition sensor 34 is positioned. As the medication 36 passes, the sensor scans it to determine its composition. The scan information is compared to the information about the target medication in memory to ensure the correct medication for this individual was dispensed.

Figure 17:
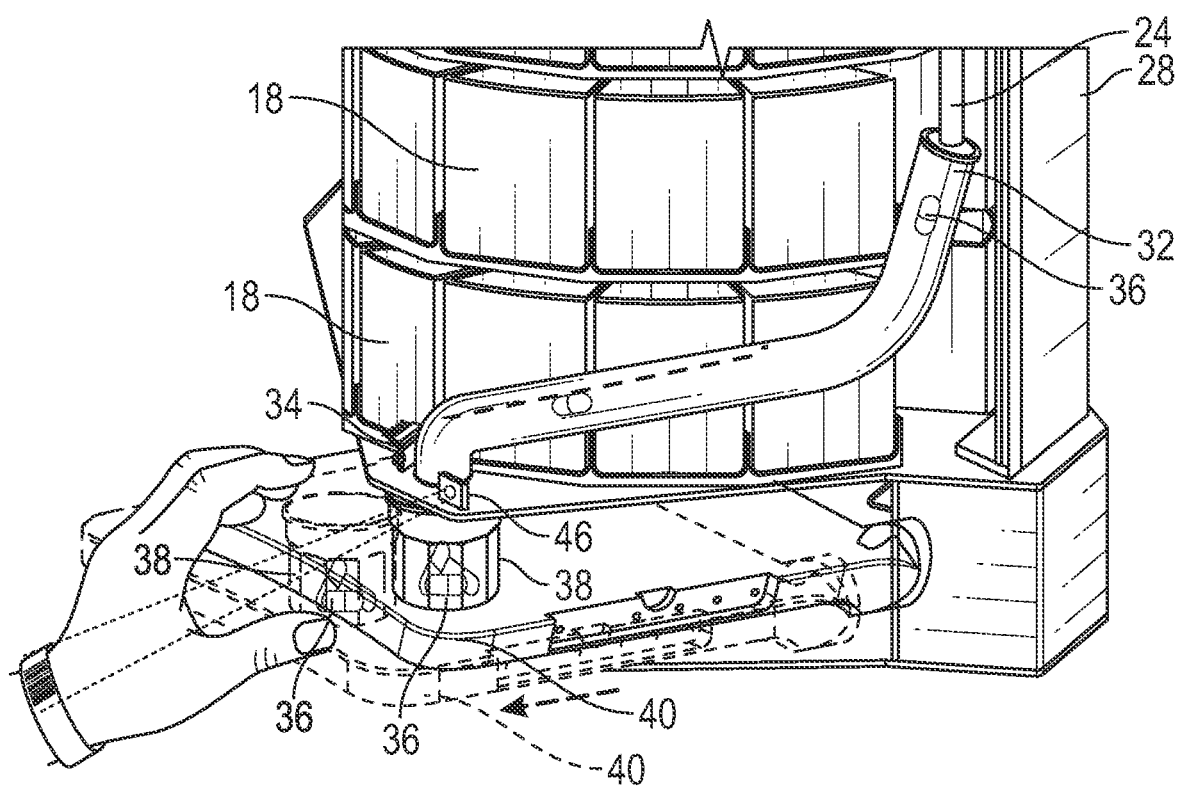
FIG. 17 is an enlarged front view of a portion of the medication dispenser and showing the medication dropping into a dispensing cup, constructed and operative in accordance with the present invention.

Thereafter the medication 36 drops into a cup 38 or another suitable receptacle as shown in FIG. 17. In a preferred embodiment, the cup 38 is situated on a movable tray 40. To facilitate access to the cup with the medication the tray may slide out. When pushed all the way in, the cup 38 aligns with the exit tube 32 to catch and retain the medication 36. For easy access, the tray can then be pulled out.

An external or internal memory module is electronically connected to the robot and contains optical recognition scans and personal information of persons located within said premises, and substantive information of said designated items.

Included on the robot is optical recognition scanner 42.

A control module is in electronic communication with the means for autonomously moving, said optical recognition scanners, the memory and the means for dispensing. Typically, these electronic components will be included on an IC board 44 (FIG. 2) inside the robot along with the memory chip. The control unit directs the means for autonomously moving to move the robotic device within said premises, directs the optical recognition scanners 42 to scan persons as they are encountered, compares images from the optical recognition scanners to optical recognitions in the memory to identify said person. Upon identifying a person, the control unit searches the personal information of the person in the memory and identifies designated items specified for the person, and then directs the means for dispensing to dispense the designated item to the person.

As an additional safeguard, the device further comprising a secondary recognition scanner; and the memory module further containing secondary recognition scans of persons located within said premises; and, wherein, prior to dispensing the designated item, the control unit directs the secondary recognition scanners to scan the person, compares images from the secondary recognition scanners to secondary recognitions in the memory to confirm the person is the correct person to receive the designated item. In some embodiments, the optical recognition scanner 42 can also be used as the secondary recognition scanner, or a second optical scanner can be used.

It may be appreciated that the correct person receives the correct medication. Serious medical consequences, and even death, can occur if a person gets the wrong medication. Accordingly, in a preferred embodiment, an additional scanner 46 (FIG. 17) is provided by the exit tube. In this manner, the robotic device can confirm that the person receiving the medication is in fact the correct person. Instead of optical scanners 42 and 46, other scanners may be used, such as eye scanners, fingerprint scanners, facial scanners, and other technology. As shown in FIG. 17, the scanner 46 reads a magnetic code on a wrist band of the recipient of the medication.

Therefore, in a preferred embodiment, secondary recognition scanners may be magnetic code readers, facial scanners or fingerprint scanners or eye scanners or optical scanners and said secondary recognition scans of persons located within said memory may be magnetic codes, fingerprint scans or eye scans or facial scans or optical scans. In some embodiments, the optical recognition scanners 42 can also be used.

Another important aspect is to make sure the correct medication is selected. Therefore, it is important to double check to make sure the correct medication is in the dispenser. For this purpose, scanners are affixed to the dispenser. Prior to the vacuum tube 24 removing the designated item, this scanner scans the item to confirm its substance. In the marketplace, there are any number of scanners that can determine the composition and make up of a medication.

Therefore, preferably, the means for dispensing further comprises substantive scanners 48 (FIG. 13) and the memory module further contains substantive scans of said designated items; and, wherein, prior to dispensing the designated item, the control unit directs the substantive scanners to scan the designated item, compares scans from the substantive scanners to substantive scans in the memory to confirm the designated item is the correct designated item for the person.

Still another safety implementation is to include still another scanning system. This scanner 50 (FIG. 4) is used when the dispenser is filled in order to make sure an authorized person is filling the dispenser. This helps to ensure that the correct medication is in the correct compartment. Depending on the configuration of the robot, optical recognition scanner 42 or additional optical scanner 50 can be used, or still another scanner can be implemented on the robot. It may be appreciated that the specific location of the additional scanner is dependent on the specific configuration of the robot. The only limitation is that it must necessarily have a clear sight line to the person requiring the medication.

Therefore, preferably, the storage means further comprising supplemental recognition scanners; and the memory module further containing supplemental recognition scans of persons authorized to add items to the storage means; and, wherein, prior to adding items to the storage means, the control unit directs the supplemental scanners to scan persons attempting to add items to the storage means, compares scans from the supplemental scanners to supplemental scans in the memory to confirm the persons attempting to add items to the storage means are authorized to add items to the storage means.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

Unless specifically stated otherwise, as apparent from the preceding discussions, it is appreciated that, throughout the specification, discussions utilizing terms such as "processing," "computing," "calculating," "determining," or the like, refer to the action and/or processes of a general purpose computer of any type, such as a client/server system, mobile computing devices, smart appliances, cloud computing units or similar electronic computing devices that manipulate and/or transform data within the computing system's registers and/or memories into other data within the computing system's memories, registers or other such information storage, transmission or display devices.

Embodiments of the present invention may include apparatus for performing the operations herein. This apparatus may be specially constructed for the desired purposes, or it may comprise a computing device or system typically having at least one processor and at least one memory, selectively activated or reconfigured by a computer program stored in the computer. The resultant apparatus when instructed by software may turn the general purpose computer into inventive elements as discussed herein. The instructions may define the inventive device in operation with the computer platform for which it is desired. Such a computer program may be stored in a computer readable storage medium, such as, but not limited to, any type of disk, including optical disks, magnetic-optical disks, read-only memories (ROMs), volatile and non-volatile memories, random access memories (RAMs), electrically programmable read-only memories (EPROMs), electrically erasable and programmable read only memories (EEPROMs), magnetic or optical cards, Flash memory, disk-on-key or any other type of media suitable for storing electronic instructions and capable of being coupled to a computer system bus. The computer readable storage medium may also be implemented in cloud storage.

Some general purpose computers may comprise at least one communication element to enable communication with a data network and/or a mobile communications network.

The processes and displays presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the invention as described herein.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A mobile robot device for distributing designated items, said mobile robot device comprising:

a memory module storing person images each with an associated identification and information on associated designated items for at least one person;

a first optical recognition scanner to scan and to provide an image of an encountered person as said mobile robot device approaches said encountered person;

a control unit to compare images from said first optical recognition scanner with said person images and to identify said encountered person and their associated designated items accordingly;

a second optical scanner to scan and provide an image of said encountered person for said control unit to confirm that said identified encountered person is the correct person to receive said associated designated items;

a release mechanism to release said associated designated items according to said encountered person identification;

a third optical recognition scanner to scan said released associated designated items for said control unit to check that said scanned released designated items are the correct associated designated items for said encountered person before said release mechanism dispenses said associated designated items to said encountered person.

2. A mobile robot device according to claim 1, wherein said designated items are pharmaceutical products.

3. A device for dispensing designated items integrated with a mobile robot device, said device comprising:

at least one storage compartment storing designated items;

at least one scanner to scan to scan and to provide an image of an encountered person as said mobile robot device approaches said encountered person;

a vacuum tube to suck designated items out of said at least one storage compartment;

a control unit to compare images from said at least one scanner with said person images and to identify said encountered person and their associated designated items accordingly, said control unit to direct said vacuum tube to said at least one storage compartment according to said associated designated items and to activate a vacuum in said vacuum tube;

a mobile arm to move said vacuum tube from said at least one storage compartment to an exit tube and to indicate to said control unit to release said associated items into said exit tube;

a scanner to scan said released associated designated items for said control unit to check that said scanned released designated items are the correct associated designated items for said encountered person; and a container to receive said designated items from said exit tube.

4. A device according to claim 3 wherein said designated items are pharmaceutical products.

5. An autonomously moving robotic device for distributing designated items to designated persons, comprising:

multiple compartments for containing designated items;

release mechanism to release items from said multiple compartments;

an external or internal memory module containing optical recognition scans and personal information of persons located within a premises, and substantive information of said designated items;

optical recognition scanners;

a control module in electronic communication with said optical recognition scanners, said memory and said release mechanism; and, wherein, said control unit directs said robotic device to move within said premises, directs said optical recognition scanners to scan persons as they are encountered, compares images from said optical recognition scanners to optical recognitions in said memory to identify said person; and, wherein, upon identifying said person, said control unit searches said personal information of said person in said memory and identifies designated items specified for said person, and then directs said release mechanism to release said designated item to said person; and, said device further comprising secondary recognition scanners; and, said memory module further containing secondary recognition scans of persons located within said premises; and, wherein, prior to releasing said designated item, said control unit directs said secondary recognition scanners to scan said person, compares images from said secondary recognition scanners to secondary recognitions in said memory to confirm said person is the correct person to receive said designated item.

6. A robotic device according to claim 5, wherein said designated items are pharmaceutical products.

7. A robotic device according to claim 5 wherein said device further comprising secondary recognition scanners; and, said memory module further containing secondary recognition scans of persons located within said premises; and, wherein, prior to dispensing said designated item, said control unit directs said secondary recognition scanners to scan said person, compares images from said secondary recognition scanners to secondary recognitions in said memory to confirm said person is the correct person to receive said designated item.

8. A robotic device according to claim 7, wherein said secondary recognition scanners being magnetic code readers, fingerprint scanners or eye scanners or facial scanners or optical scanners and said secondary recognition scans of persons located within said memory being magnetic codes, fingerprint scans or eye scans or facial scans or optical scans.

9. A robotic device according to claim 5, wherein said release mechanism further comprising substantive scanners and said memory module further containing substantive scans of said designated items; and, wherein, prior to dispensing said designated item, said control unit directs said substantive scanners to scan said designated item, compares scans from said substantive scanners to substantive scans in said memory to confirm said designated item is the correct designated item for said person.

10. A robotic device according to claim 5 wherein said device further comprising supplemental recognition scanners; and, said memory module further containing supplemental recognition scans of persons authorized to add items to said multiple compartments; and, wherein, prior to adding items to said multiple compartments, said control unit directs said supplemental scanners to scan persons attempting to add items to said multiple compartments, compares scans from said supplemental scanners to supplemental scans in said memory to confirm said persons attempting to add items to said multiple compartments are authorized to add items to said multiple compartments.

11. An autonomously moving robotic device for distributing designated items to designated persons, comprising:

multiple compartments for containing designated items;

release mechanism to release items from said multiple compartments;

an external or internal memory module containing optical recognition scans and personal information of persons located within said premises, and substantive information of said designated items;
optical recognition scanners;
a control module in electronic communication with said optical recognition scanners, said memory and said release mechanism; and,
wherein, said control unit directs said robotic device to move within said premises, directs said optical recognition scanners to scan persons as they are encountered, compares images from said optical recognition scanners to optical recognitions in said memory to identify said person; and
wherein, upon identifying said person, said control unit searches said personal information of said person in said memory and identifies designated items specified for said person, and then directs said release mechanism to release said designated item to said person; and,
wherein said release mechanism further comprising substantive scanners and said memory module further containing substantive scans of said designated items; and, wherein, prior to releasing said designated item, said control unit directs said substantive scanners to scan said designated item, compares scans from said substantive scanners to substantive scans in said memory to confirm said designated item is the correct designated item for said person.

12. A robotic device according to claim 11, wherein said designated items are pharmaceutical products.

13. A robotic device according to claim 11, wherein said device further comprising secondary recognition scanners; and, said memory module further containing secondary recognition scans of persons located within said premises; and, wherein, prior to releasing said designated item, said control unit directs said secondary recognition scanners to scan said person, compares images from said secondary recognition scanners to secondary recognitions in said memory to confirm said person is the correct person to receive said designated item.

14. A robotic device according to claim 13, wherein said secondary recognition scanners being magnetic code readers, fingerprint scanners or eye scanners or facial scanners or optical scanners and said secondary recognition scans of persons located within said memory being magnetic codes, fingerprint scans or eye scans or facial scans or optical scans.

15. A robotic device according to claim 11, wherein said release mechanism further comprising substantive scanners and said memory module further containing substantive scans of said designated items; and, wherein, prior to releasing said designated item, said control unit directs said substantive scanners to scan said designated item, compares scans from said substantive scanners to substantive scans in said memory to confirm said designated item is the correct designated item for said person.

16. A robotic device according to claim 11, wherein said multiple compartments further comprising supplemental recognition scanners; and, said memory module further containing supplemental recognition scans of persons authorized to add items to said multiple compartments; and, wherein, prior to adding items to said multiple compartments, said control unit directs said supplemental scanners to scan persons attempting to add items to said multiple compartments, compares scans from said supplemental scanners to supplemental scans in said memory to confirm said persons attempting to add items to said multiple compartments are authorized to add items to said multiple compartments.

17. An autonomously moving robotic device for distributing designated items to designated persons, comprising:
multiple compartments for containing designated items;
release mechanism to release items from said multiple compartments;
an external or internal memory module containing optical recognition scans and personal information of persons located within said premises, and substantive information of said designated items;
optical recognition scanners;
a control module in electronic communication with said optical recognition scanners, said memory and said release mechanism; and,
wherein, said control unit directs said robotic device to move within said premises, directs said optical recognition scanners to scan persons as they are encountered, compares images from said optical recognition scanners to optical recognitions in said memory to identify said person; and
wherein, upon identifying said person, said control unit searches said personal information of said person in said memory and identifies designated items specified for said person, and then directs said release mechanism to release said designated item to said person; and,
supplemental recognition scanners; and, said memory module further containing supplemental recognition scans of persons authorized to add items to said multiple compartments; and, wherein, prior to adding items to said multiple compartments, said control unit directs said supplemental scanners to scan persons attempting to add items to said multiple compartments, compares scans from said supplemental scanners to supplemental scans in said memory to confirm said persons attempting to add items to said multiple compartments are authorized to add items to said multiple compartments.

18. A robotic device according to claim 17, wherein said designated items are pharmaceutical products.

19. A robotic device according to claim 17, wherein said device further comprising secondary recognition scanners; and, said memory module further containing secondary recognition scans of persons located within said premises; and, wherein, prior to dispensing said designated item, said control unit directs said secondary recognition scanners to scan said person, compares images from said secondary recognition scanners to secondary recognitions in said memory to confirm said person is the correct person to receive said designated item.

20. A robotic device according to claim 19, wherein said secondary recognition scanners being magnetic code readers, fingerprint scanners or eye scanners or facial scanners or optical scanners and said secondary recognition scans of persons located within said memory being magnetic codes, fingerprint scans or eye scans or facial scans or optical scans.

21. A robotic device according to claim 17, wherein said release mechanism further comprising substantive scanners and said memory module further containing substantive scans of said designated items; and, wherein, prior to releasing said designated item, said control unit directs said substantive scanners to scan said designated item, compares scans from said substantive scanners to substantive scans in said memory to confirm said designated item is the correct designated item for said person.

* * * * *